(12) United States Patent
Baines et al.

(10) Patent No.: US 11,269,114 B2
(45) Date of Patent: Mar. 8, 2022

(54) GEOLOGICAL DATA ASSESSMENT SYSTEM

(71) Applicant: Landmark Graphics Corporation, Houston, TX (US)

(72) Inventors: Graham Baines, Abingdon (GB); Benjamin S. Saunders, Stanford in the Vale (GB); Graeme Richard Nicoll, East Hendred (GB); Jean-Christophe Wrobel-Daveau, Wantage (GB)

(73) Assignee: Landmark Graphics Corporation, Houston, TX (US)

(*) Notice: Subject to any disclaimer, the term of this patent is extended or adjusted under 35 U.S.C. 154(b) by 107 days.

(21) Appl. No.: 16/787,564

(22) Filed: Feb. 11, 2020

(65) Prior Publication Data

US 2020/0174158 A1    Jun. 4, 2020

Related U.S. Application Data

(63) Continuation of application No. PCT/US2018/036308, filed on Jun. 6, 2018.

(51) Int. Cl.
*G01V 99/00*    (2009.01)
*G01V 1/24*    (2006.01)
*G06N 7/00*    (2006.01)

(52) U.S. Cl.
CPC .............. *G01V 99/005* (2013.01); *G01V 1/24* (2013.01); *G06N 7/005* (2013.01); *G01V 2210/6224* (2013.01); *G01V 2210/661* (2013.01); *G01V 2210/665* (2013.01); *G01V 2210/74* (2013.01)

(58) Field of Classification Search
CPC ......... G01V 99/005; G01V 1/24; G06N 7/005
See application file for complete search history.

(56) References Cited

U.S. PATENT DOCUMENTS

| 10,473,817 | B2* | 11/2019 | Theune ............... G01V 99/005 |
| 2003/0216897 | A1 | 11/2003 | Endres et al. | |
| 2010/0175886 | A1* | 7/2010 | Bohacs ............... G01V 99/005 166/369 |
| 2011/0098930 | A1 | 4/2011 | Pyrcz et al. | |
| 2015/0316668 | A1 | 11/2015 | Kolbjørnsen et al. | |
| 2016/0370482 | A1 | 12/2016 | Mallet et al. | |
| 2017/0175492 | A1 | 6/2017 | Harris et al. | |

OTHER PUBLICATIONS

International Search Report and Written Opinion dated Feb. 21, 2019, International PCT Application No. PCT/US2018/036308.

* cited by examiner

*Primary Examiner* — Bryan Bui
(74) *Attorney, Agent, or Firm* — McGuireWoods LLP

(57) ABSTRACT

The disclosed embodiments include systems and methods to assess geological data. The method includes obtaining data associated with a geological state of a geological entity. The method also includes assessing a nature of a geological age constraint of the geological entity. The method further includes generating a first probability distribution of a geological age of the geological entity based on the nature of the geological age constraint of the geological entity. The method further includes selecting a time of interest for analysis of the geological entity. The method further includes assessing a nature of the geological age constraint during the time of interest. The method further includes generating a second probability distribution for the time of interest. The method further includes determining a likelihood that the geological age constraint of the geological entity coincides with the time of interest.

20 Claims, 4 Drawing Sheets

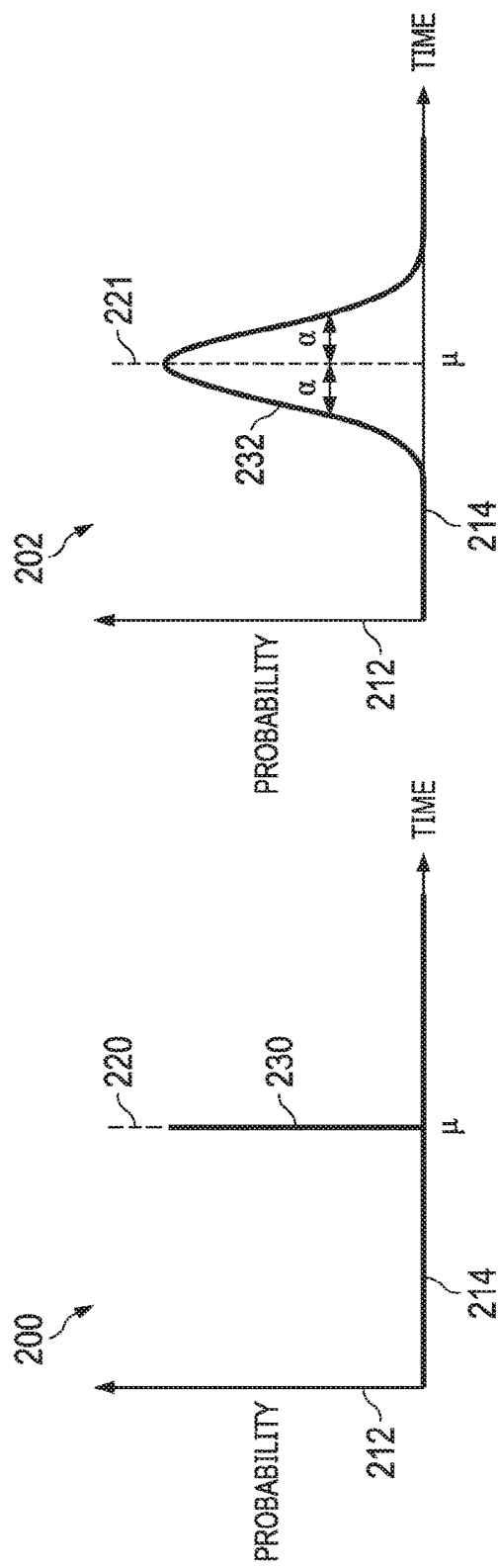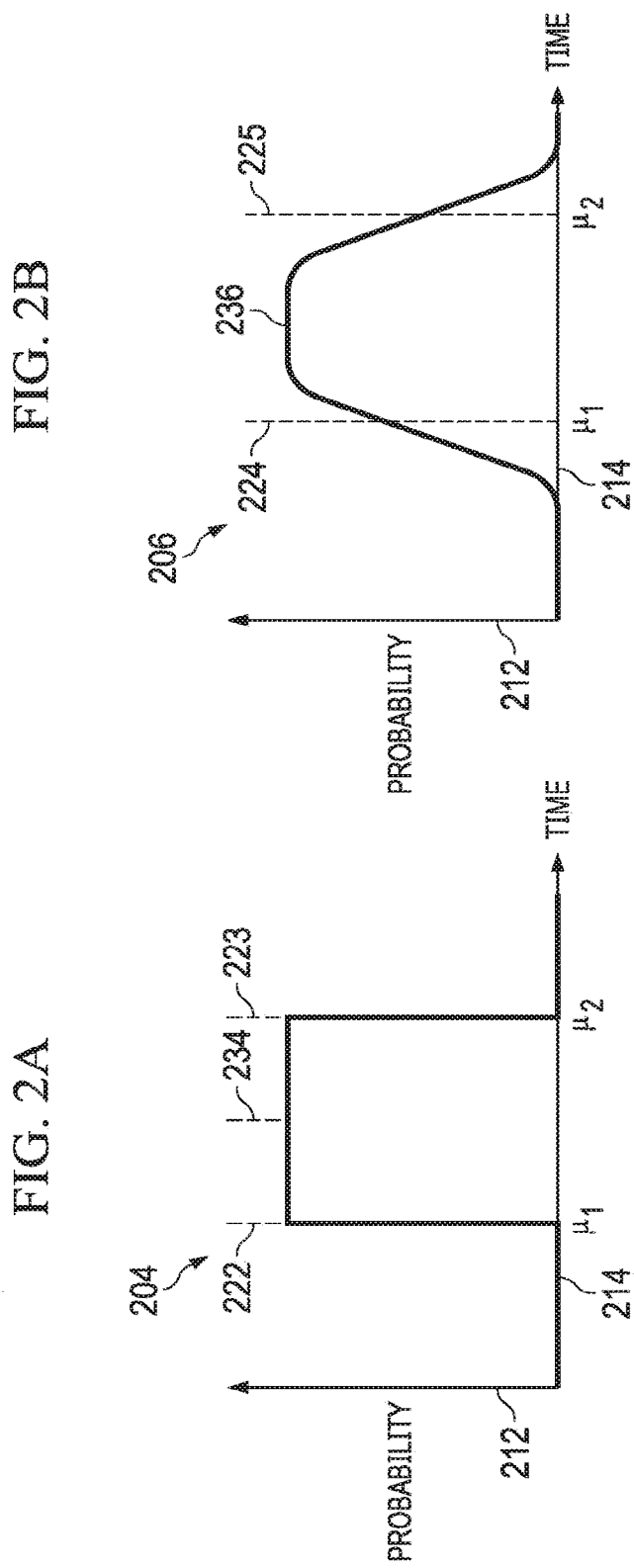

GEOLOGICAL DATA ASSESSMENT SYSTEM

CROSS-REFERENCE TO RELATED APPLICATIONS

This application is a Continuation of International Application No. PCT/US2018/036308, filed Jun. 6, 2018, which is hereby incorporated by reference in its entirety.

BACKGROUND

The present disclosure relates generally to systems and methods to assess temporal relevance of geological data.

Geoscientists sometimes synthesize geological data to interpret the geological state of the earth at a particular geological time. Geoscientists often synthetize geological data based on a temporal attribution associated with the geological data. The temporal attribution may encompass time spans from thousands of years to tens or hundreds of millions of years. Further, different techniques for selecting the temporal attribution may cause the time span associated with the temporal attribution to vary. Further, Geoscientists sometimes make different geological observations of geological data at a particular time, which further complicates the process to assess the geological data.

BRIEF DESCRIPTION OF THE DRAWINGS

Illustrative embodiments of the present disclosure are described in detail below with reference to the attached drawing figures, which are incorporated by reference herein, and wherein:

FIG. 2A is a graph illustrating a probability distribution of a geological age of a geological entity, where the time of interest for an analysis of the geological entity is an exact instant;

FIG. 2B is a graph illustrating a probability distribution of a geological age of a second geological entity, where the time of interest for an analysis of the second geological entity is an inexact instant;

FIG. 2C is a graph illustrating a probability distribution of a geological age of a third geological entity, where the time of interest for an analysis of the third geological entity is an exact instant;

FIG. 2D is a graph illustrating a probability distribution of a geological age of a fourth geological entity, where the time of interest for an analysis of the fourth geological entity is an inexact internal with upper and lower limits defined by inexact ages;

Figure 1:
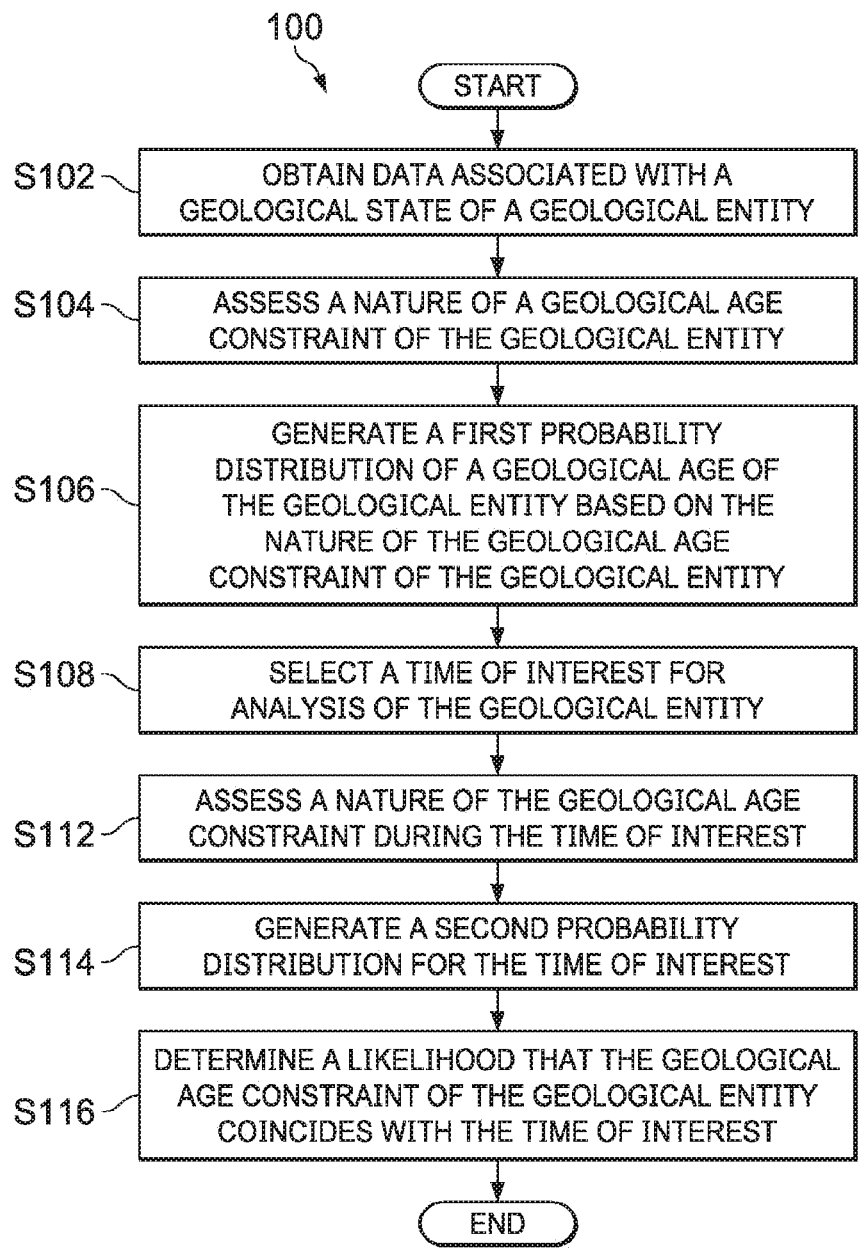
FIG. 1 is a flow chart of a process to assess temporal relevance of geological data.

The illustrated figures are only exemplary and are not intended to assert or imply any limitation with regard to the environment, architecture, design, or process in which different embodiments may be implemented.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

The present disclosure relates to systems and methods to assess temporal relevance of geological data. More particularly, the present disclosure relates to systems and methods to determine a likelihood that a geological entity's age constraint coincides with a time of interest of the geological entity. As used herein, a geological entity refers to any geological unit of the earth. Examples of geological entities include, but are not limited to mineral deposits, hydrocarbon deposits, fossils, or any other geological units. Further, and as used herein, a time of interest refers to a point in time or a time frame for analyzing the geological entity.

The geological data assessment system (hereafter referred to as system) described herein has access to databases that host geological data (hereafter referred to database or collectively as databases). The system obtains data associated with a geological state of a geological entity, such as, for example, hydrocarbon deposit. Examples of a geological state of a geological entity include, but are not limited to the age of the geological entity, the material properties of the geological entity, the period of time the geological entity was deposited on another geological entity, as well as other quantifiable natures of the geological entity. The system assesses a nature of a geological constraint of the geological entity and generates a probability distribution of a geological age of the geological entity based on the nature of the geological age constraint of the geological entity. The system also selects a time of interest for analysis of the geological entity. In some embodiments, the system detects a user input that includes the time of interest and uses the inputted time of interest for analysis of the geological entity. The system assesses a nature of the geological age constraint during the time of interest and generates another probability distribution for the time of interest. The system then determines the likelihood that the geological age constraint of the geological entity coincides with the time of interest. Additional descriptions of the foregoing systems and methods to assess temporal relevance of geological data are described in the paragraphs below and are illustrated in FIGS. 1-4.

Now turning to the figures, FIG. 1 is a flow chart of a process 100 to assess temporal relevance of geological data. The process may be performed by the geological data assessment system described herein, including the geological data assessment system illustrated in FIG. 3, or one or more processors of the geological data assessment system. Although the operations in the process 100 are shown in a particular sequence, certain operations may be performed in different sequences or at the same time where feasible. As described below, process 100 provides an intuitive way for assessing temporal relevance of geological data.

Figure 3:
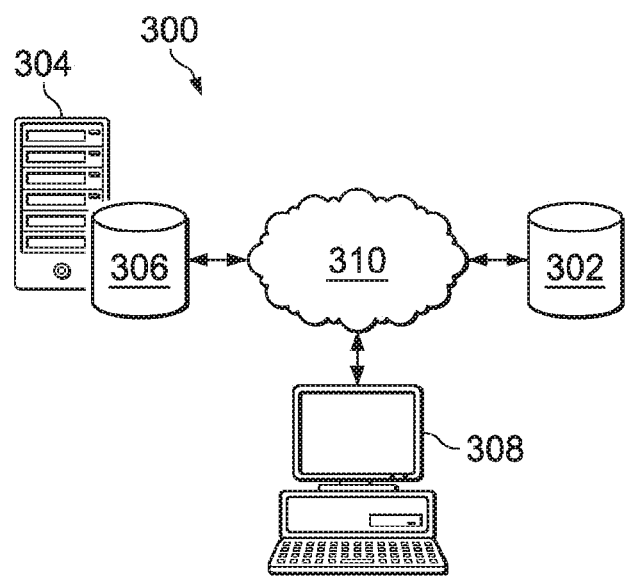
FIG. 3 is a network environment for assessing temporal relevance of geological data.

A processor of a geological data assessment system (processor), such as the geological data assessment system 304 of FIG. 3, at block S102, obtains data associated with a geological state of a geological entity. In some embodiments, data associated with the geological entity are stored in a remote database, such as database 302 of FIG. 3. In other embodiments, data associated with the geological entity are stored locally, such as on storage medium 306 of FIGS. 3 and 4. At block S104, the processor assesses a nature of a geological age constraint of the geological entity. In some embodiments, the geological age constraint of the geological entity is a point in time, such as 70,000,000 B.C. In other embodiments, the geological age constraint of the geological entity is a period of time, such as between 80,000,000 B.C. and 60,000,000 B.C.

At block S106, the processor generates a first probability distribution of a geological age of the geological entity based on the nature of the geological age constraint of the geological entity. In some embodiments, the probability distribution of the geological age of the geological entity is a probability mass distribution. In such embodiments, the processor generates a probability mass distribution of the geological age of the geological entity over time. In other embodiments, the probability distribution of the geological age of the geological entity is a probability density distribution. In such embodiments, the processor generates a probability density distribution of the geological age of the geological entity over time. In further embodiments, the probability distribution is based on a combination of the probability mass distribution and the probability density distribution of the geological entity's age. In such embodiments, the processor generates a probability mass distribution and a probability density distribution of the geological entity and generates a probability distribution of the geological age of the geological entity based on both the geological mass distribution and the geological density distribution of the geological entity's age.

In some embodiments, where the geological age constraint of the geological entity is a point in time (e.g., 70,000,000 B.C.), the generated probability distribution is a probability that the geological state of the geological entity occurred at the point in time. For example, where the geological age constraint of 70,000,000 B.C. represents the instant that a material was deposited on the earth's crust as the result of an asteroid impact, then e.g., the processor generates a probability distribution that represents the likelihood that the material was deposited on the earth at 70,000,000 B.C. In other embodiments, where the geological age constraint of the geological entity is a period of time (e.g., between 80,000,000 B.C. and 60,000,000 B.C.), the processor assigns at least two points in time (e.g., 80,000,000 B.C., and 60,000,000 B.C., respectively) as boundaries of the period of time. The processor then generates a probability distribution that the geological age constraint of the geological entity is satisfied between the first boundary and the second boundary. For example, where the geological entity is a layer of limestone, and the two points in time represents two boundaries of time the layer limestone was deposited on another layer of limestone, then the probability distribution represents the likelihood that the layer of limestone was deposited between 80,000,000 B.C., and 60,000,000 B.C. In one or more of such embodiments, the processor generates a probability distribution that has a mean likelihood that the geological age constraint of the geological entity is satisfied between the first boundary and the second boundary. In one or more of such embodiments, the processor generates a probability distribution that has a threshold standard deviation of likelihood or another threshold likelihood (e.g., two standard deviations, half a standard deviation, or another threshold likelihood) that the geological age constraint of the geological entity is satisfied between the first boundary and the second boundary. In one or more embodiments, where the geological age constraint of a geological entity occurred at inexact intervals, the processor assigns multiple points in time as different boundaries of time. For example, where the geological entity is a dyke that cuts sediments that were deposited between a first inexact interval, but is overlain by a conglomerate that was deposited between a second inexact interval that occurred after the first inexact interval, the processor assigns four points in time to define boundaries of the first inexact interval and the boundaries of the second inexact interval. In one or more of such embodiments, the processor generates a probability distribution of the likelihood of the foregoing scenario would be satisfied between the boundaries of the first inexact interval and the second inexact interval. In one or more of such embodiments, the probability distribution represents a probability distribution having a threshold standard deviation of likelihood that the geological age constraint of the geological entity is satisfied between the boundaries of the first and the second inexact time intervals. Additional examples of operations performed by the processor to select the geological age constraint are illustrated in at least FIGS. 2A-2E and are described in the paragraphs below.

At block S108, the processor selects a time of interest for analysis of the geological entity. In one or more embodiments, the processor detects a user input (e.g., from an analyst) that includes the time of interest. In other embodiments, the processor automatically selects a time of interest based on prior analysis of similar geological entities. At block S112, the processor generates a second probability distribution for the time of interest. In some embodiments, the probability distribution of the time of interest is a probability mass distribution. In such embodiments, the processor generates a probability mass distribution of the time of interest. In other embodiments, the probability distribution of the time of interest is a probability density distribution. In such embodiments, the processor generates a probability density distribution of the time of interest. In further embodiments, the probability distribution is based on a combination of the probability mass distribution and the probability density distribution of the time of interest. In such embodiments, the processor generates a probability mass distribution and a probability density distribution of the time of interest and generates a probability distribution of the geological age of the geological entity based on both the geological mass distribution and the geological density distribution of the time of interest.

At block S114, the processor determines a likelihood that the geological age constraint of the geological entity coincides with the time of interest. In some embodiments, the processor integrates the first probability distribution with the second probability distribution to determine the likelihood that the geological age of the geological entity is within the time of interest. Additional examples of the process for determining the likelihood that a geological age constraint of a geological entity coincides with a time of interest are provided in the paragraphs below and are illustrated in at least FIGS. 2A-2E. In some embodiments, the processor also generates a model that is indicative of the likelihood that the geological age constraint of the geological entity coincides with the time of interest and provides the model for display on a display of an electronic device, such as the electronic device of the analyst. In one or more embodiments, the processor is also operable of receiving additional user inputs (e.g., from the analyst), such a new time of interest, to fine tune the generated model or to generate new models based on new inputs from the analyst.

FIG. 2A is a graph 200 illustrating a probability distribution 230 of a geological age of a geological entity, where the time of interest for an analysis of the geological entity is an exact instant. In the illustrated embodiment, axis 214 represents time and axis 212 represents the probability of the geological age of the geological entity at a given time. Line 220 represents a point in time $\mu$. In the illustrated embodiment, the geological age of the geological entity is an exact instant, at time $\mu$. As such, the probability distribution 230 falls entirely on line 220.

In some embodiments, where the time of interest for an analysis of the geological entity is an exact instant, the geological data assessment system utilizes the following equation to calculate the probability distribution:

$$P(t) = \begin{cases} 1, & \mu = t_1 \\ 0, & \mu \neq t_1 \end{cases} \quad \text{Eq. 1}$$

where P(t) is the probability distribution over time, $\mu$ is a point in time, and time t1 is the time of interest. In this embodiment, the data of the geological entity matches the time of interest exactly when the data is 100% relevant to the time of interest. For all other cases the data is irrelevant for the time of interest.

FIG. 2B is another graph 202 illustrating a probability distribution 232 of a geological age of a second geological entity, where the time of interest for an analysis of the second geological entity is an inexact instant. In the illustrated embodiment, axis 214 represents time and axis 212 represents the probability of the geological age of the geological entity at a given time. Line 221 represents a point in time $\mu$. Further, $\sigma$ represents a standard deviation from the point in time $\mu$.

In some embodiments, where the time of interest for an analysis of the geological entity is an inexact instant, the geological data assessment system utilizes the following equation to calculate the probability distribution:

$$P(t) = \frac{1}{\sigma \sqrt{2\pi}} e^{-\frac{(t_1 - \mu)^2}{2\sigma^2}}, \quad \text{Eq. 2}$$

where P(t) is the probability distribution over time, $\mu$ is a point in time, $\sigma$ is a standard deviation from the point in time $\mu$, and time t1 is the time of interest.

For example, if a lava has a U-Pb zircon age of 87±1 (2 $\sigma$), the probability that lava erupted at 86.3 Ma may be determined by entering the foregoing parameters into equation 2 as follows:

$$P = \frac{1}{0.5\sqrt{2\pi}} e^{-\frac{(86.3-87)^2}{2(0.5)^2}} = 0.299.$$

FIG. 2C is a graph 204 illustrating a probability distribution 234 of a geological age of a third geological entity (e.g., the deposition age of a sandstone bed), where the time of interest for an analysis of the third geological entity is an exact interval of time. In the illustrated embodiment, axis 214 represents time and axis 212 represents the probability of the geological age of the geological entity at a given time. Line 222 represents a point in time $\mu_1$ that defines one boundary (e.g., lower boundary) of an interval of time and line 223 represents a second point in time $\mu_2$ that defines a second boundary (e.g., upper boundary) of the interval of time.

In some embodiments, where the time of interest for an analysis of the geological entity is an exact interval of time, the geological data assessment system utilizes the following equation to calculate the probability distribution:

$$P(t) = \begin{cases} \frac{1}{\mu_2 - \mu_1}, & \mu_1 \leq t_1 \leq \mu_2 \\ 0, & t_1 < \mu_1 \\ 0, & t_1 > \mu_2 \end{cases}, \quad \text{Eq. 3}$$

where P(t) is the probability distribution over time, $\mu_1$ is a first boundary of an interval of time $\mu_2$ is a second boundary of an interval of time, and time t1 is the time of interest.

For example, if a sandstone bed is known to have deposited between 66 Ma and 86 Ma, the probability that it deposited at 70 Ma may be determined by entering the foregoing parameters into equation 3 as follows:

$$P(t) = \frac{\text{Area}}{\text{Width}} = \frac{1}{\text{Data Interval}} = \frac{1}{\mu_2 - \mu_1} = \frac{1}{86 - 66} = 0.05 = 5\%.$$

FIG. 2D is a graph 206 illustrating a probability distribution 236 of a geological age of a fourth geological entity (e.g., a conglomerate unconformably overlies a granite that intruded at a first inexact time interval, the conglomerate is itself intruded by a dyke at a second inexact time interval), where the time of interest for an analysis of the fourth geological entity is an inexact internal with upper and lower limits defined by inexact ages. In the illustrated embodiment, axis 214 represents time and axis 212 represents the probability of the geological age of the geological entity at a given time. Line 224 represents a point in time $\mu_1$ that defines a first point in time around which an inexact time interval is defined (e.g., the inexact time interval of the granite). Line 225 represents a second point in time $\mu_2$ that defines a second point in time around which a second inexact time interval is defined (e.g., the inexact time interval the conglomerate was intruded by the dyke).

In some embodiments, where the time of interest for an analysis of the geological entity is an inexact internal with upper and lower limits defined by inexact ages, the geological data assessment system utilizes the following equation to calculate the probability distribution:

$$P = \frac{1}{4(\mu_2 - \mu_1)} \left[ 1 + \text{erf}\left( \frac{t_1 - \mu_1}{\sigma_{\mu_1} \sqrt{2}} \right) \right] \left[ 1 - \text{erf}\left( \frac{t_1 - \mu_2}{\sigma_{\mu_2} \sqrt{2}} \right) \right], \quad \text{Eq. 4}$$

where $\mu_1$ is a first point in time around which an inexact time interval is defined, $\mu_2$ is a second point in time around which a second inexact time interval is defined, $\sigma_{\mu 1}$ is the standard deviation from the point in time $\mu_1$, $\sigma_{\mu 2}$ is the standard deviation from the point in time $\mu_2$, and time t1 is the time of interest.

Continuing with the foregoing example, if a conglomerate unconformably overlies a granite that intruded 86±8 Ma (2σ), the conglomerate is itself intruded by a dyke at 66±6 Ma (2σ), the probability that it deposited at 70 Ma may be determined by entering the foregoing parameters into equation 4 as follows:

$$P = \frac{1}{4(86-66)}\left[1+\text{erf}\left(\frac{70-66}{3\sqrt{2}}\right)\right]\left[1-\text{erf}\left(\frac{70-86}{4\sqrt{2}}\right)\right],$$

which simplifies to ⅟₈₀ [1+0.818] [1+1.000]=0.0455=4.55%.

Figure 2E:
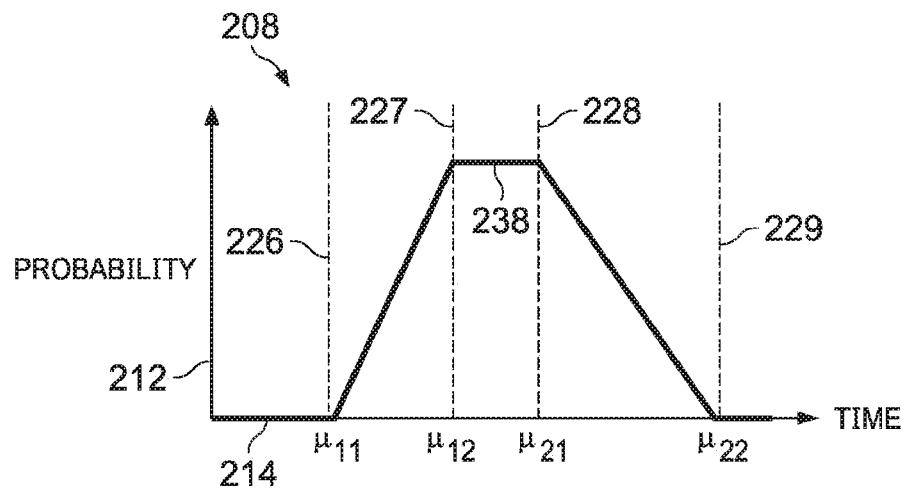
FIG. 2E is a graph illustrating a probability distribution of a geological age of a fifth geological entity, where the time of interest for an analysis of the fifth geological entity is an inexact internal with upper and lower limits defined by two inexact intervals.

FIG. 2E is a graph 208 illustrating a probability distribution 238 of a geological age of a fifth geological entity, where the time of interest for an analysis of the fifth geological entity is an inexact internal with upper and lower limits defined by inexact intervals. For example, the geological entity is a dyke, the dyke cuts sediments that deposited between a first inexact interval, but is overlain by a conglomerate that deposited between a second inexact interval. In the illustrated embodiment, axis 214 represents time and axis 212 represents the probability of the geological age of the geological entity at a given time. Line 226 represents a point in time $\mu_{11}$ that defines a first boundary of a first inexact time interval (e.g., the inexact time interval of the sediments were deposited). Line 227 represents a second point in time $\mu_{12}$ that defines a second boundary of the first inexact time interval. Line 228 represents a point in time $\mu_{21}$ that defines a first boundary of a second inexact time interval (e.g., the inexact time interval of the conglomerate was deposited). Line 229 represents a second point in time $\mu_{22}$ that defines a second boundary of the second inexact time interval.

In some embodiments, where the time of interest for an analysis of a geological entity is an inexact internal with upper and lower limits defined by two inexact intervals, the geological data assessment system utilizes the following equation to calculate the probability distribution:

$$P(t) = \begin{cases} 0 & t_1 < \mu_{11} \\ c\left(\frac{t_1 - \mu_{11}}{\mu_{12} - \mu_{11}}\right), & \mu_{11} \leq t_1 \leq \mu_{12} \\ c, & \mu_{12} < t_1 \leq \mu_{21} \\ c\left(\frac{t_1 - \mu_{22}}{\mu_{21} - \mu_{22}}\right), & \mu_{21} < t_1 \leq \mu_{22} \\ 0, & t_1 > \mu_{22} \end{cases} \quad \text{Eq. 5}$$

Where $c = \left(\frac{2}{\mu_{21} + \mu_{22} - \mu_{11} - \mu_{12}}\right)$, $\mu_{11}$ is a point in time that defines a first boundary of a first inexact time interval, $\mu_{12}$ is a second point in time that defines a second boundary of the first inexact time interval, $\mu_{21}$ is a point in time that defines a first boundary of a second inexact time interval, $\mu_{22}$ is a point in time that defines a second boundary of the second inexact time interval, and time t1 is the time of interest.

Continuing with the foregoing example, if a dyke cuts sediments that deposited between 78 Ma and 94 Ma, but is overlain by a conglomerate that deposited between 61 Ma and 71 Ma, the probability that the dyke intruded 70 Ma may be determined by entering the foregoing parameters into equation 5 as follows:

$$c = \frac{2}{\mu_{21} + \mu_{22} - \mu_{11} - \mu_{12}} = \frac{2}{78 + 94 - 61 - 71} = \frac{1}{20} \text{ and}$$

$$P(t) = \begin{cases} 0 & \cancel{70 < 61} \\ \frac{1}{20}\left(\frac{70-61}{71-61}\right) = 0.045, & 61 \leq 70 \leq 71 \\ \frac{1}{20}, & \cancel{71 < 70 \leq 78} \\ \cancel{\frac{2}{20}\left(\frac{70-94}{78-94}\right) = 0.075}, & \cancel{78 < 70 \leq 94} \\ \cancel{0,} & \cancel{70 > 94} \end{cases}$$

Although the foregoing paragraphs and FIGS. 2A-2E illustrate some examples for determining the likelihood that a geological age constraint of a geological entity coincides with a time of interest, the geological data assessment system may select other suitable geological age constraints or other geological entities, and to utilize other suitable methods to determine the likelihood of the geological age constraint of a geological entity coincides with a time of interest.

FIG. 3 is a network environment 300 for assessing temporal relevance of geological data.

The network environment 300 includes a geological data assessment system 304 that is communicatively connected to an electronic device 308 and a database 302 via a network 310.

Geological data are stored in database 302. Database 302 may be formed from data storage components such as, but not limited to, read-only memory (ROM), random access memory (RAM), flash memory, magnetic hard drives, solid state hard drives, CD-ROM drives, DVD drives, floppy disk drives, as well as other types of data storage components and devices. In some embodiments, the database 302 includes multiple data storage devices. In further embodiments, the multiple data storage devices may be physically stored at different locations. In one of such embodiments, the data storage devices are components of a server station, such as a cloud server. In another one of such embodiments, the data storage devices are components of the geological data assessment system 304.

The geological data assessment system 304 obtains geological data associated with a geological state of a geological entity from the database 302. Examples of geological data assessment systems include work management stations, server systems, desktop computers, laptop computers, tablet computers, smartphones, smart watches, PDAs, as well as other electronic devices having hardware and software components operable to assess temporal relevance of geological data. The geological data assessment system 304 includes or is communicatively connected to a storage medium 306. The geological data assessment system 304 temporarily or permanently stores geological data associated with the geological entity on storage medium 306. Additional descriptions of the storage medium 306 are provided in the paragraphs below. The geological data assessment system 304 then assesses a nature of a geological age constraint of the geological entity and generates a first probability distribution of a geological age of the geological entity based on the nature of the geological age constraint of the geological entity. The geological data assessment system 304 also selects a time of interest for analysis of the geological entity and assesses a nature of the geological age constraint during the time of interest, and generates a second probability distribution for the time of interest. The geological data assessment system 304 then determines, based on the first probability distribution and the second probability distribution, a likelihood that the geological age constraint of the geological entity coincides with the time of interest. Detailed descriptions of certain processes performed by geological data assessment system 304 are provided in the paragraphs above and are illustrated in FIG. 1.

In the illustrated embodiment, the geological data assessment system 304 also generates a model of the likelihood that the geological age constraint coincides with time of interest and provides the model to electronic device 308. Examples of the electronic device 308 include work management stations, server systems, desktop computers, laptop computers, tablet computers, smartphones, smart watches, PDAs, as well as similar electronic devices having a processor operable to provide data indicative of the temporal relevance of geological data for display. In the illustrated embodiment, the electronic device 308, upon receipt of the model, provides the mode for display on a display of the electronic device 308. An analyst operating the electronic device 308 may enter additional inputs to request the geological data assessment system 304 to generate additional models or to fine tune the generated model. In one or more embodiments, where the analyst operates the geological data assessment system 304, models indicative of the likelihood that the geological age constraint coincides with time of interest are displayed on a display of the geological data assessment system 304.

Figure 4:
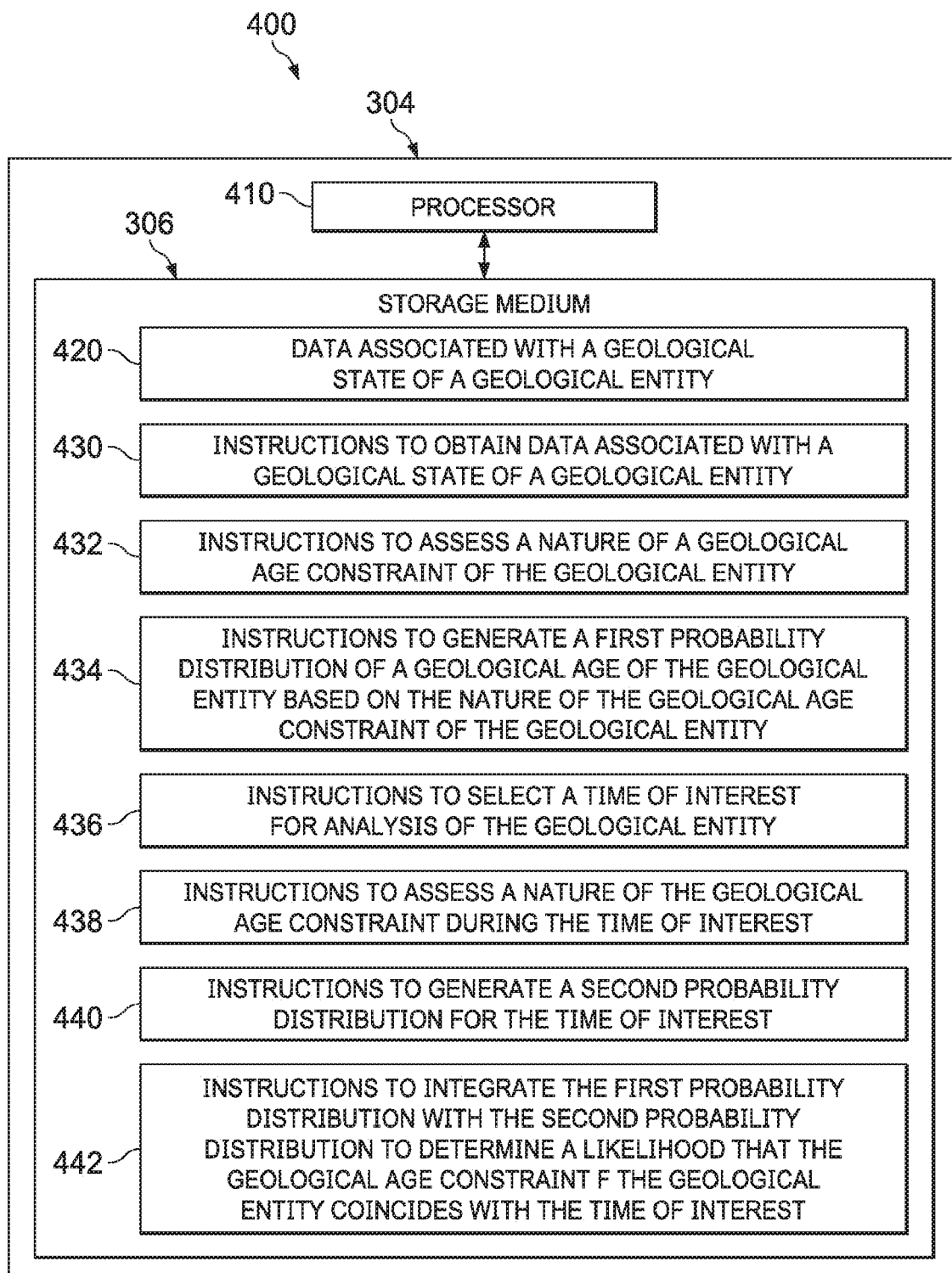
FIG. 4 is a block diagram of the geological data assessment system of FIG. 3 that is operable of performing operations illustrated in the process of FIG. 1 to assess temporal relevance of geological data.

FIG. 4 is a block diagram of the geological data assessment system 304 of FIG. 3, where the geological data assessment system 304 is operable of performing the operations illustrated in process 100 of FIG. 1 to assess temporal relevance of geological data. The geological data assessment system 304 includes the storage medium 306 of FIG. 3 and a processor 410. The storage medium 306 may be formed from data storage components such as, but not limited to, read-only memory (ROM), random access memory (RAM), flash memory, magnetic hard drives, solid state hard drives, CD-ROM drives, DVD drives, floppy disk drives, as well as other types of data storage components and devices. In some embodiments, the storage medium 306 includes multiple data storage devices. In further embodiments, the multiple data storage devices may be physically stored at different locations. Data indicative of measurements obtained from external databases that contain geological data, such as database 302 of FIG. 3, are transmitted to the geological data assessment system 304 and are stored at a first location 420 of the storage medium. In one or more embodiments, where temporal relevance of a geological entity is being performed, data associated with geological states of the geological entity are stored at the first location 420 of the storage medium 306. As shown in FIG. 4, instructions to obtain data associated with a geological state of a geological entity are stored in a second location 430. Further, instructions to assess the nature of a geological age constraint of the geological entity are stored in a third location 432. Further, instructions to generate a first probability distribution of a geological age of the geological entity based on the nature of the geological age constraint of the geological entity are stored at a fourth location 434. Further, instructions to select a time of interest for analysis of the geological entity are stored at a fifth location 436. Further, instructions to assess a nature of a geological age constraint during the time of interest are stored at sixth location 438. Further, instructions to generate a second probability distribution for the time of interest are stored at a seventh location 440. Further, instructions to integrate the first probability distribution with the second probability distribution to determine a likelihood that the geological age constraint of the geological entity coincides with the time of interest are stored at an eighth location 442. Further additional instructions that are performed by the processor 410 are stored in other locations of the storage medium 306.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/processes may be performed in parallel or out of sequence, or combined into a single step/process. The scope of the claims is intended to broadly cover the disclosed embodiments and any such modification. Further, the following clauses represent additional embodiments of the disclosure and should be considered within the scope of the disclosure.

Clause 1, a method to assess temporal relevance of geological data, the method comprising: obtaining data associated with a geological state of a geological entity; assessing a nature of a geological age constraint of the geological entity; generating a first probability distribution of a geological age of the geological entity based on the nature of the geological age constraint of the geological entity; selecting a time of interest for analysis of the geological entity; assessing a nature of the geological age constraint during the time of interest; generating a second probability distribution for the time of interest; and determining a likelihood that the geological age constraint of the geological entity coincides with the time of interest.

Clause 2, the method of clause 1, further comprising integrating the first probability distribution with the second probability distribution to determine the likelihood that the geological age of the geological entity is within the time of interest.

Clause 3, the method of clause 1 or clause 2, wherein generating the first probability distribution of the geological age of the geological entity comprises generating at least one of a probability mass distribution of the geological age of the geological entity over time and a probability density function of the geological age of the geological entity over time.

Clause 4, the method of any of clauses 1-3, wherein generating the second probability distribution of the time of interest comprises generating at least one of a probability mass distribution of the time of interest and a probability density distribution of the time of interest.

Clause 5, the method of any of clauses 1-4, wherein the geological age constraint of the geological entity is a point in time, and wherein the first probability distribution of the geological age of the geological entity is a probability that the geological state of the geological entity occurred at the point in time.

Clause 6, the method of any of clauses 1-5, further comprising: assigning a first boundary that is associated with a first point in time; and assigning a second boundary that is associated with a second point in time that occurred after the first point in time, wherein generating the first probability distribution comprises generating a probability distribution having a mean likelihood that the geological age constraint of the geological entity is satisfied between the first boundary and the second boundary.

Clause 7, the method of any of clauses 1-6, wherein generating the first probability distribution comprises generating a probability distribution having a threshold standard deviation of likelihood that the geological age constraint of the geological entity is satisfied between the first boundary and the second boundary.

Clause 8, the method of any of clauses 1-6, further comprising: assigning a third boundary that is associated with a third point in time that occurred prior to the first point in time; and assigning a fourth boundary that is associated with a fourth point in time that occurred after the second point in time, wherein generating the first probability distribution comprises generating a probability distribution having a threshold standard deviation of likelihood that the geological age constraint of the geological entity is satisfied between the third boundary and the fourth boundary.

Clause 9, the method of any of clauses 1-8, further comprising: generating a model of the likelihood that the geological entity's age constraint coincides with the time of interest; and providing the model for display on a display of an electronic device.

Clause 10, a geological data assessment system, comprising: memory storing data associated with a geological state of a geological entity; and a processor operable to: obtain data associated with a geological state of a geological entity; assess a nature of a geological age constraint of the geological entity; generate a first probability distribution of a geological age of the geological entity based on the nature of the geological age constraint of the geological entity; select a time of interest for analysis of the geological entity; assess a nature of the geological age constraint during the time of interest; generate a second probability distribution for the time of interest; and determine, based on the first probability distribution and the second probability distribution, a likelihood that the geological age constraint of the geological entity coincides with the time of interest.

Clause 11, the geological data assessment system of clause 10, wherein the processor is further operable to integrate the first probability distribution with the second probability distribution to determine the likelihood that the geological age constraint falls within the time of interest.

Clause 12, the geological data assessment system of clause 10 or 11, wherein the processor is further operable to generate at least one of a probability mass distribution of the geological age of the geological entity and a probability density distribution of the geological age of the geological entity, wherein at least one of the probability mass distribution and the probability density distribution is the first probability distribution.

Clause 13, the geological data assessment system of any of clauses 10-12, wherein the processor is further operable to generate at least one of a probability mass distribution of the time of interest and a probability density distribution of the time of interest, wherein the at least one of the probability mass distribution and the probability density distribution is the second probability distribution.

Clause 14, the geological data assessment system of any of clauses 10-13, wherein the geological age constraint of the geological entity is a point in time, and wherein the first probability distribution of the geological age of the geological entity is a probability that the geological state of the geological entity occurred at the point in time.

Clause 15, the geological data assessment system of any of clauses 10-14, wherein the geological age constraint of the geological entity is an interval of time having a first boundary associated with a first point in time and a second boundary associated with a second point in time that occurred after the first point in time, and wherein the first probability distribution of the geological age of the geological entity is a probability that the geological state of the geological entity occurred between the first point in time and the second point in time.

Clause 16, the geological data assessment system of any of clauses 10-15, wherein the geological age constraint of the geological entity is an interval of time having a third boundary associated with a third point in time that occurred before the first point in time, and a fourth boundary associated with a fourth point in time that occurred after the second point in time, and wherein the first probability distribution of the geological age of the geological entity is a probability that the geological state of the geological entity occurred between the third point in time and the fourth point in time.

Clause 17, the geological data assessment system of any of clauses 10-16, wherein the processor is further operable to: generate a model of the likelihood that the geological age constraint coincides with time of interest; and provide the model for display on the display of an electronic device.

Clause 18, a machine-readable medium comprising instructions stored therein, which when executed by one or more processors, causes the one or more processors to perform operations comprising: obtaining data associated with a geological state of a geological entity; assessing a nature of a geological age constraint of the geological entity; generating a first probability distribution of a geological age of the geological entity based on the nature of the geological age constraint of the geological entity; selecting a time of interest for analysis of the geological entity; assessing a nature of the geological age constraint during the time of interest; generating a second probability distribution for the time of interest; and integrating the first probability distribution with the second probability distribution to determine a likelihood that the geological age constraint of the geological entity coincides with the time of interest.

Clause 19, the machine-readable medium of claim 18, further comprising instructions stored therein, which when executed by one or more processors, causes the one or more processors to perform operations comprising: assigning a first boundary that is associated with a first point in time; and assigning a second boundary that is associated with a second point in time that occurred after the first point in time, wherein generating the first probability distribution comprises generating a probability distribution having a mean likelihood that the geological age constraint of the geological entity is satisfied between the first boundary and the second boundary.

Clause 20, the machine-readable medium of clause 18 or 19, further comprising instructions stored therein, which when executed by one or more processors, cause the one or more processors to perform operations comprising: generating a model of the likelihood that the geological age constraint coincides with time of interest; and providing the model for display on the display of an electronic device.

Although certain embodiments disclosed herein describes transmitting electrical currents from electrodes deployed on an inner string to electrodes deployed on an outer string, one of ordinary skill would understand that the subject technology disclosed herein may also be implemented to transmit electrical currents from electrodes deployed on the outer string to electrodes deployed on the inner string.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

What is claimed is:

1. A method to assess temporal relevance of geological data, the method comprising:
   obtaining data associated with a geological state of a geological entity;
   assessing a nature of a geological age constraint of the geological entity;
   generating a first probability distribution of a geological age of the geological entity based on the nature of the geological age constraint of the geological entity;
   selecting a time of interest for analysis of the geological entity;
   assessing a nature of the geological age constraint during the time of interest;
   generating a second probability distribution for the time of interest; and
   determining a likelihood that the geological age constraint of the geological entity coincides with the time of interest, wherein the time of interest refers to a point in time or a time frame for analyzing the geological entity.

2. The method of claim 1, further comprising integrating the first probability distribution with the second probability distribution to determine the likelihood that the geological age of the geological entity is within the time of interest.

3. The method of claim 1, wherein generating the first probability distribution of the geological age of the geological entity comprises generating at least one of a probability mass distribution of the geological age of the geological entity over time and a probability density function of the geological age of the geological entity over time.

4. The method of claim 1, wherein generating the second probability distribution of the time of interest comprises generating at least one of a probability mass distribution of the time of interest and a probability density distribution of the time of interest.

5. The method of claim 1, wherein the geological age constraint of the geological entity is a point in time, and wherein the first probability distribution of the geological age of the geological entity is a probability that the geological state of the geological entity occurred at the point in time.

6. The method of claim 1, further comprising:
   assigning a first boundary that is associated with a first point in time; and
   assigning a second boundary that is associated with a second point in time that occurred after the first point in time,
   wherein generating the first probability distribution comprises generating a probability distribution having a mean likelihood that the geological age constraint of the geological entity is satisfied between the first boundary and the second boundary.

7. The method of claim 6, wherein generating the first probability distribution comprises generating a probability distribution having a threshold standard deviation of likelihood that the geological age constraint of the geological entity is satisfied between the first boundary and the second boundary.

8. The method of claim 6, further comprising:
   assigning a third boundary that is associated with a third point in time that occurred prior to the first point in time; and
   assigning a fourth boundary that is associated with a fourth point in time that occurred after the second point in time,
   wherein generating the first probability distribution comprises generating a probability distribution having a threshold standard deviation of likelihood that the geological age constraint of the geological entity is satisfied between the third boundary and the fourth boundary.

9. The method of claim 1, further comprising:
   generating a model of the likelihood that the geological entity's age constraint coincides with the time of interest; and
   providing the model for display on a display of an electronic device.

10. A geological data assessment system, comprising:
    memory storing data associated with a geological state of a geological entity; and
    a processor operable to:
       obtain data associated with a geological state of a geological entity;
       assess a nature of a geological age constraint of the geological entity;
       generate a first probability distribution of a geological age of the geological entity based on the nature of the geological age constraint of the geological entity;
       select a time of interest for analysis of the geological entity;
       assess a nature of the geological age constraint during the time of interest;
       generate a second probability distribution for the time of interest; and
       determine, based on the first probability distribution and the second probability distribution, a likelihood that the geological age constraint of the geological entity coincides with the time of interest,
       wherein the time of interest refers to a point in time or a time frame for analyzing the geological entity.

11. The geological data assessment system of claim 10, wherein the processor is further operable to integrate the first probability distribution with the second probability distribution to determine the likelihood that the geological age constraint falls within the time of interest.

12. The geological data assessment system of claim 10, wherein the processor is further operable to generate at least one of a probability mass distribution of the geological age of the geological entity and a probability density distribution of the geological age of the geological entity, wherein at least one of the probability mass distribution and the probability density distribution is the first probability distribution.

13. The geological data assessment system of claim 10, wherein the processor is further operable to generate at least one of a probability mass distribution of the time of interest and a probability density distribution of the time of interest, wherein the at least one of the probability mass distribution and the probability density distribution is the second probability distribution.

14. The geological data assessment system of claim 10, wherein the geological age constraint of the geological entity is a point in time, and wherein the first probability distribution of the geological age of the geological entity is a probability that the geological state of the geological entity occurred at the point in time.

15. The geological data assessment system of claim 10, wherein the geological age constraint of the geological entity is an interval of time having a first boundary associated with a first point in time and a second boundary associated with a second point in time that occurred after the first point in time, and wherein the first probability distribution of the geological age of the geological entity is a probability that the geological state of the geological entity occurred between the first point in time and the second point in time.

16. The geological data assessment system of claim 15, wherein the geological age constraint of the geological entity is an interval of time having a third boundary associated with a third point in time that occurred before the first point in time, and a fourth boundary associated with a fourth point in time that occurred after the second point in time, and wherein the first probability distribution of the geological age of the geological entity is a probability that the geological state of the geological entity occurred between the third point in time and the fourth point in time.

17. The geological data assessment system of claim 10, wherein the processor is further operable to:
generate a model of the likelihood that the geological age constraint coincides with time of interest; and
provide the model for display on the display of an electronic device.

18. A machine-readable medium comprising instructions stored therein, which when executed by one or more processors, causes the one or more processors to perform operations comprising:
obtaining data associated with a geological state of a geological entity;
assessing a nature of a geological age constraint of the geological entity;
generating a first probability distribution of a geological age of the geological entity based on the nature of the geological age constraint of the geological entity;
selecting a time of interest for analysis of the geological entity;
assessing a nature of the geological age constraint during the time of interest;
generating a second probability distribution for the time of interest; and
integrating the first probability distribution with the second probability distribution to determine a likelihood that the geological age constraint of the geological entity coincides with the time of interest,
wherein the time of interest refers to a point in time or a time frame for analyzing the geological entity.

19. The machine-readable medium of claim 18, further comprising instructions stored therein, which when executed by one or more processors, causes the one or more processors to perform operations comprising:
assigning a first boundary that is associated with a first point in time; and
assigning a second boundary that is associated with a second point in time that occurred after the first point in time,
wherein generating the first probability distribution comprises generating a probability distribution having a mean likelihood that the geological age constraint of the geological entity is satisfied between the first boundary and the second boundary.

20. The machine-readable medium of claim 18, further comprising instructions stored therein, which when executed by one or more processors, cause the one or more processors to perform operations comprising:
generating a model of the likelihood that the geological age constraint coincides with time of interest; and
providing the model for display on the display of an electronic device.

* * * * *